United States Patent [19]
Gresl et al.

[11] Patent Number: 5,397,335
[45] Date of Patent: Mar. 14, 1995

[54] TROCAR ASSEMBLY WITH IMPROVED ADAPTER SEALS

[75] Inventors: Charles Gresl, San Francisco; Edwin Hlavka, Palo Alto, both of Calif.

[73] Assignee: Origin Medsystems, Inc., Menlo Park, Calif.

[21] Appl. No.: 93,101

[22] Filed: Jul. 13, 1993

[51] Int. Cl.⁶ .............................................. A61M 5/00
[52] U.S. Cl. ..................................... 606/185; 604/167
[58] Field of Search ............... 604/167, 160, 161, 164, 604/165, 168, 169, 158, 159, 178, 264, 272, 51; 606/184, 185

[56] References Cited

U.S. PATENT DOCUMENTS

| | | |
|---|---|---|
| 4,442,836 | 4/1988 | Meinecke . |
| 5,104,383 | 4/1992 | Shichman . |
| 5,112,321 | 5/1992 | Hiltebrandt ........................ 604/167 |
| 5,211,633 | 5/1993 | Stouder, Jr. ........................ 604/167 |
| 5,221,264 | 6/1993 | Wilk et al. ............................ 604/256 |
| 5,224,930 | 7/1993 | Spaeth et al. ........................ 604/164 |

FOREIGN PATENT DOCUMENTS 312219 4/1989 European Pat. Off. .
479130 4/1992 European Pat. Off. .

Primary Examiner—Stephen C. Pellegrino
Assistant Examiner—William Lewis
Attorney, Agent, or Firm—Heller, Ehrman, White & McAuliffe

[57] ABSTRACT

The present invention is directed to a medical device for performing endoscopic procedures comprising a trocar and a cannula assembly having slidable adapter seals. The cannula assembly has a housing at the proximal extracorporeal end of a cannula. A generally semicircular track follows the periphery of the cannula housing and at least one adapter seal slidably is engaged with the track. The adapter seal comprises a plate that accommodates a sealing element with an aperture for receiving surgical instruments. The adapter seal has engagement means for maintaining the adapter seal in the track. In addition, the adapter seal has releasing means that can be acted upon to apply a counteringforce against a tensioning means in order to remove the adapter seal from the cannula assembly.

22 Claims, 4 Drawing Sheets

TROCAR ASSEMBLY WITH IMPROVED ADAPTER SEALS

BACKGROUND OF THE INVENTION

This invention relates to a surgical instrument for use in endoscopic procedures and, in particular, to a trocar assembly having improved adapter seals for accommodating differently sized surgical instruments.

Trocars are surgical instruments that have found wide application in many types of procedures where puncture-type incisions are to be made; in particular, insufflatory surgery. Insufflatory surgery involves filling a body cavity with a pressurized gas to maintain the cavity under a certain pre-determined pressure. In such surgery, a trocar is used to puncture the body cavity by inserting the trocar through a cannula or sheath. After the incision is made by the trocar, the cannula is partially inserted into the body cavity through the incision. The trocar is then removed from the cannula, and thereafter, other surgical instruments may be inserted through the cannula to perform various endoscopic procedures. A trocar assembly is a unit typically comprising a trocar and a cannula. Trocar assemblies are available as disposable or reusable units.

Due to the minimal invasive nature of endoscopic procedures, endoscopy is a preferred surgical approach when possible. Endoscopic surgical procedures employ a variety of surgical instruments, e.g., endoscopes, biopsy forceps, bipolar forceps, coagulation probes, etc. These surgical instruments differ in shape and size. For example, in the course of a single surgical procedure, some of the instruments used may have a cross-sectional diameter in their elongate regions on the order of 5 mm, while others may have a diameter of 10 mm or larger. The shape of the operative end of the instruments will also vary depending on their intended function. A gastight seal between the cannula and an instrument inserted therein must be maintained. A typical cannula assembly will have a flexible seal ring as a sealing means. The flexible seal ring allows instruments within a certain range of sizes to be inserted into the cannula and provides a seal with those instruments to prevent gas leakage. It is desirable to avoid removing a cannula once it has been inserted into the body, however the flexible seal ring may not be able to accommodate the various instruments to be used in performing a surgical procedure. In such cases, cannula assemblies of different sizes may be needed to accommodate the instruments. Commercially available trocar assemblies come in a range of inner diameters (e.g., 3, 5, 7, 8, 10, 11 and 12 mm sizes).

The problem of accommodating instruments of various sizes during a surgical procedure, without replacing cannulas, still remains to be addressed. Large diameter instruments simply cannot be used with a cannula having a smaller diameter. Small diameter instruments, e.g., 3 mm, are unusable in a larger size cannula, e.g., 12 mm, because the flexible seal ring in the cannula assembly is too large and cannot effectively maintain the gas pressure within the body cavity. The trocar and cannula assemblies now available for maintaining a certain gas pressure in the cavity when using differently sized surgical instruments are simply too difficult and inconvenient to use.

SUMMARY OF THE INVENTION

The present invention is directed to a medical device for performing endoscopic procedures comprising a trocar and a cannula assembly having slidable adapter seals. The cannula assembly has a housing at the proximal extracorporeal end of a cannula. A generally semicircular track follows the periphery of the cannula housing and at least one adapter seal slidably is engaged with the track. The adapter seal comprises a plate that accommodates a sealing element with an aperture for receiving surgical instruments. The adapter seal has engagement means for engaging the track. It is an object of the present invention to provide an adapter seal and tensioning means for maintaining the engagement means in the track and releasing means that can be acted upon to apply a countering-force against the tensioning means in order to remove the adapter seal from the cannula assembly.

It is also an object of the present invention to provide a cannula assembly that has multiple adapter seals which permit the use of surgical instruments of various sizes with the cannula assembly.

It is another object of the present invention to provide an adapter seal that is removable and provides an effective seal with an endoscopic surgical instrument.

It is a further object of the present invention to provide a cannula assembly that permits a large tissue specimen to be recovered.

It is another object of the present invention to provide an adapter seal that has a sealing element that has flaps that open to permit a large tissue specimen to be recovered.

It is still another object of the present invention to provide an adapter seal that has disengagable washer-like sealing element that permits a large tissue specimen to be recovered.

It is still a further object of the present to provide an adapter seal that has a disengagable gasket sealing element that permits a large tissue sample to be recovered.

These and other objects of the present invention will be apparent from the following description of the preferred embodiment and the appended claims.

DESCRIPTION OF THE PREFERRED EMBODIMENTS

The present invention allows physicians to use a variety of differently sized surgical instruments, while reducing the need to interchange cannulas of different sizes, by providing adapter seals that can accommodate differently sized surgical instruments and maintain the gas pressure in the body cavity during an endoscopic procedure.

Figure 1A:
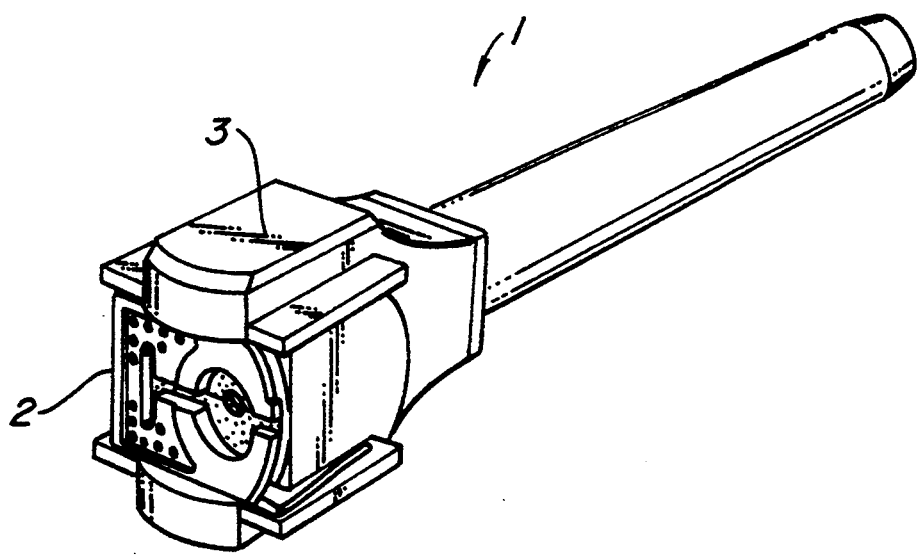
FIG. 1A is a quarter view of the present cannula assembly with an adapter seal in operative position.
Figure 1B:
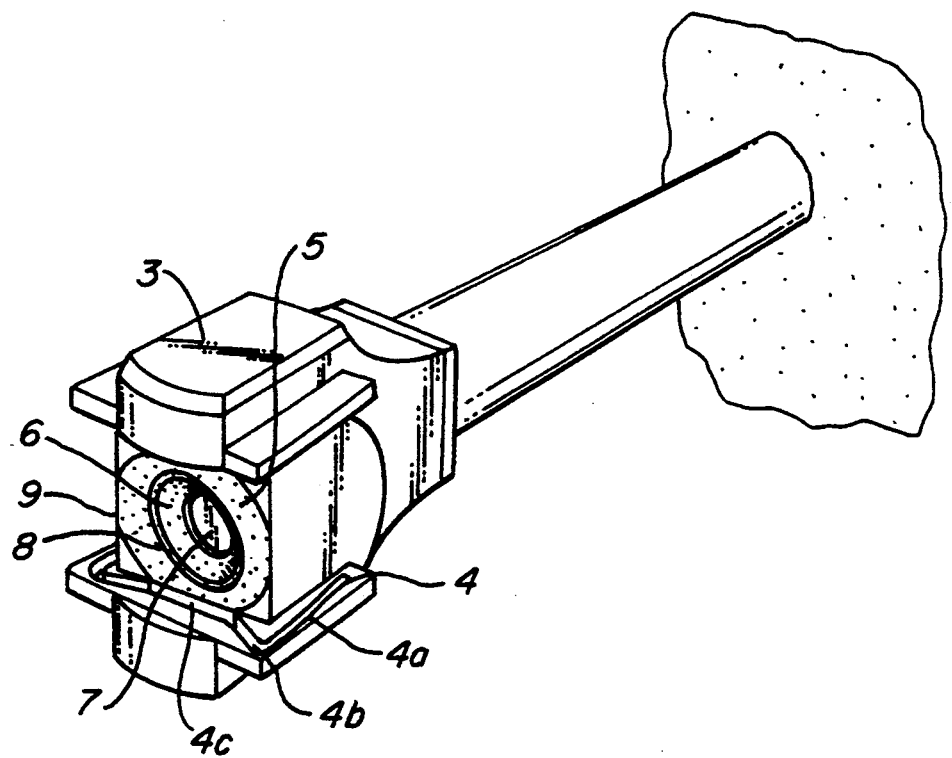
FIG. 1B shows a view of the cannula assembly with the adapter seal removed.

As shown in FIG. 1A, the cannula assembly 1 has an adapter seal 2 positioned to accept a surgical instrument. The adapter seal 2 is moved by manually sliding it in the parallel tracks that follow the outer perimeter of the cannula housing 3 which is located at the proximal extracorporeal end of the cannula assembly 1. FIG. 1B shows the cannula assembly 1 with the adapter seal 2 removed and provides an unobstructed view of the proximal extracorporeal end of the cannula assembly. The track 4 follows a path that permits an adapter seal 2 to move slidably from positions on either side of the cannula housing 3 to the operative position shown in FIG. 1A. The side portion of the track 4a is angled away from the side body of the cannula housing 3 as it approaches the corner portion of the track 4b. The corner portion 4b has a channel width that is wider than the side portion 4a of the track to enable the adapter seal to move around the corner. At the corner, the track angles back inward towards portion 4c of the track. The portion 4c of the track has an inner channel side surface that is nearly flush with the surface of main seal 5. The track follows a generally U-shaped path around the outer perimeter of the cannula housing 3. An upper track (not shown) mirrors the path of the lower track 4.

At the proximal end of the cannula assembly, there is a main seal 5. The main seal 5 has an inwardly sloping hole 6 at the center and at the edge of the hole is a seal ring 8 that protrudes from the surface of the main seal 5. The hole 6 is covered by a flapper valve 7 that can be opened by pushing a button (not shown) on the bottom of the cannula housing 3. The seal ring 8 presses against a sealing element 18 of an adapter seal 2 to form a gastight seal when the adapter seal is in the operative position.

Figure 2:
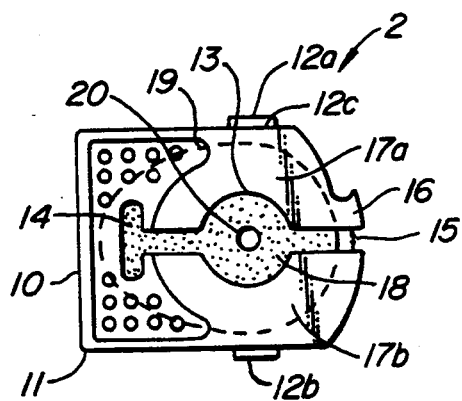
FIG. 2 is a front view of an embodiment of an adapter seal as set forth by the present inventor.

Referring to FIG. 2, the adapter seal 2 comprises a thin flat plate 11 that is preferably made of a plastic material. The plate 11 has engagement means that are shown as tabs 12a and 12b. The engagement means are located on the top and bottom edges of the plate 11. The tabs 12a and 12b engage the track 4 and permits the adapter seal 2 to slide in the channel of the track. The shape of the engagement means can be suitably varied. For example, the engagement means can be wedge shaped to facilitate disengagement from the track. Each engagement means should preferably have a flat front side surface 12c for providing cofacial contact with the channel side-surfaces of track 4 to allow the adapter seal 2 to be maintained in a stable position. Also, when an adapter seal 2 is in the operative position, the edge 10 is generally flush with edge 9 of the cannula housing.

The adapter seal 2 has an opening 13, a T-shaped opening 14 and a slot portion 15 formed in the plate 11 that together generally define arms 17a and 17b. The width of slot 15 is at least as wide as the distance that tab 12 protrudes from the top edge of the plate 11. The rigidity of the plate material and arms 17a and 17b provides the tension for maintaining the engagement means within the tracks. However, the plate material has sufficient flexibility to permit movement of the arms 17a and 17b. The plate 11 is preferably made of a polyesterimide; for example, material sold under the trademark "Ultem." The plate 11 is shown with a notch releasing means 16 for use in removing the adapter seal 2 from the cannula assembly 1. The releasing means can take the form of an extension or lever on one or both of the arms 17a and 17b that can be manipulated to squeeze close slot 15. In the embodiment shown in FIG. 2, by pressing down on the notch portion 16, the tab 12 will disengage from its track 4 and permit the removal of adapter seal 2.

The adapter seal 2 has sealing element 18 which is fitted onto and accomodated by the plate 11 of the adapter. In this embodiment, the sealing element 18 covers a substantial portion of the back side of the plate, as shown by the dotted line 19. The sealing element 18 is preferably made of a silicone rubber material. Aperture 20 in the sealing element permit a surgical instrument to be inserted through the adapter seal 2. The aperture 20 receives a surgical instrument and provides a generally gastight fit around the elongated portion of the surgical instrument. The size of aperture 20 can be varied. Also, the sealing element 18 provides resistance against the displacement of the arms 17a and 17b and provides further tension on the engagement means, e.g., tabs 12a and 12b, to remain in the track 4.

Figure 3A:
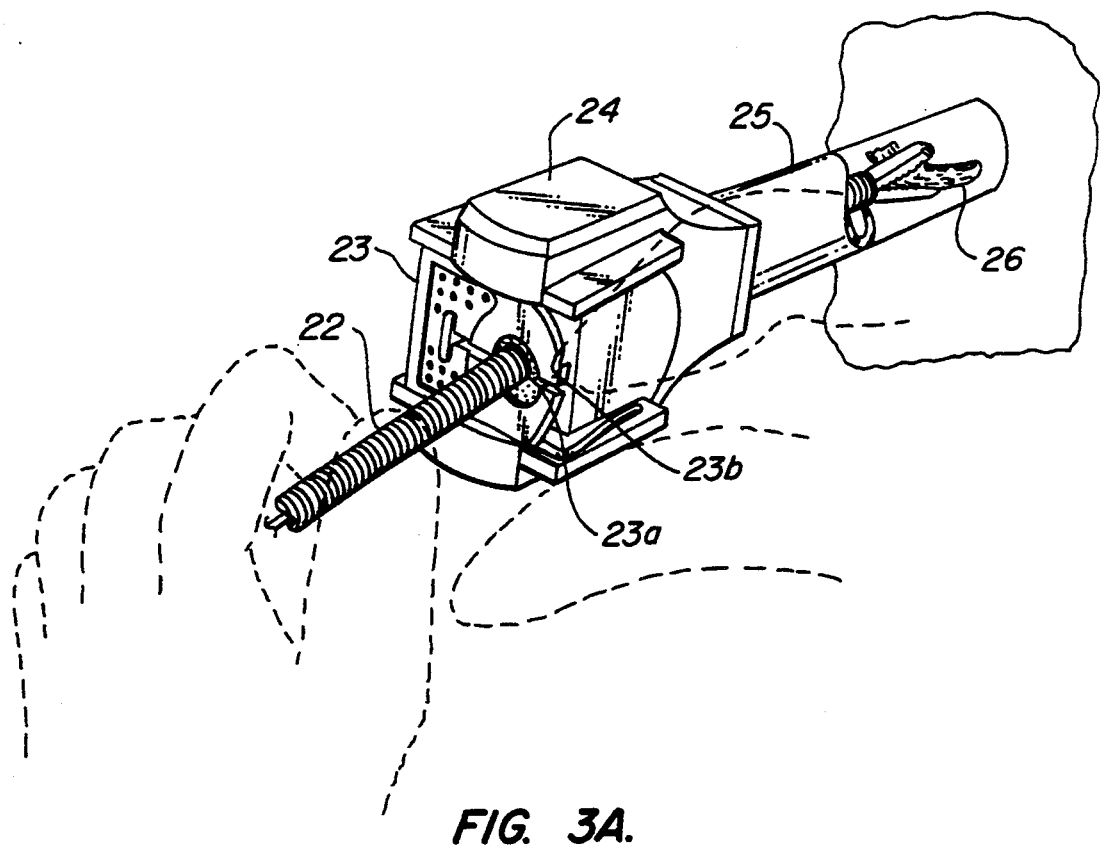
FIG. 3A is a view of the present cannula assembly being used to perform a surgical procedure wherein a surgical instrument is inserted through an adapter seal and the cannula.

Referring to FIG. 3A, a surgical instrument 22 is shown being used with the trocar assembly of the present invention. A trocar is first used to make an incision into the body cavity and is removed. Thereafter, the adapter seal 23 is slidably moved into the operative position from its position on either side of the cannula housing 24 and the surgical instrument 22 is inserted through the aperture 23a of the adapter seal and the cannula 25. The surgical instrument 22 can alternatively be inserted through the aperture while the adapter seal is detached. The adapter seal can be positioned on the track of the cannula assembly later as the surgical instrument is being inserted into the body. When in the operative position, the aperture of the adaptor seal is aligned with the longtitudinal axis of the cannula.

For example, as part of an endoscopic procedure, captured at the end of the surgical instrument 22 is a retrieved tissue specimen 26. It may be desirable, sometimes necessary, to retrieve a tissue specimen intact and that may not be possible if the specimen is pulled through the aperture of an adapter seal. By manipulating releasing means 23b, the adapter seal 23 can be disengaged from the cannula housing 24, thus making it possible to retrieve the specimen 26 without drawing it through the aperture 23a of the adapter seal 23.

Figure 3B:
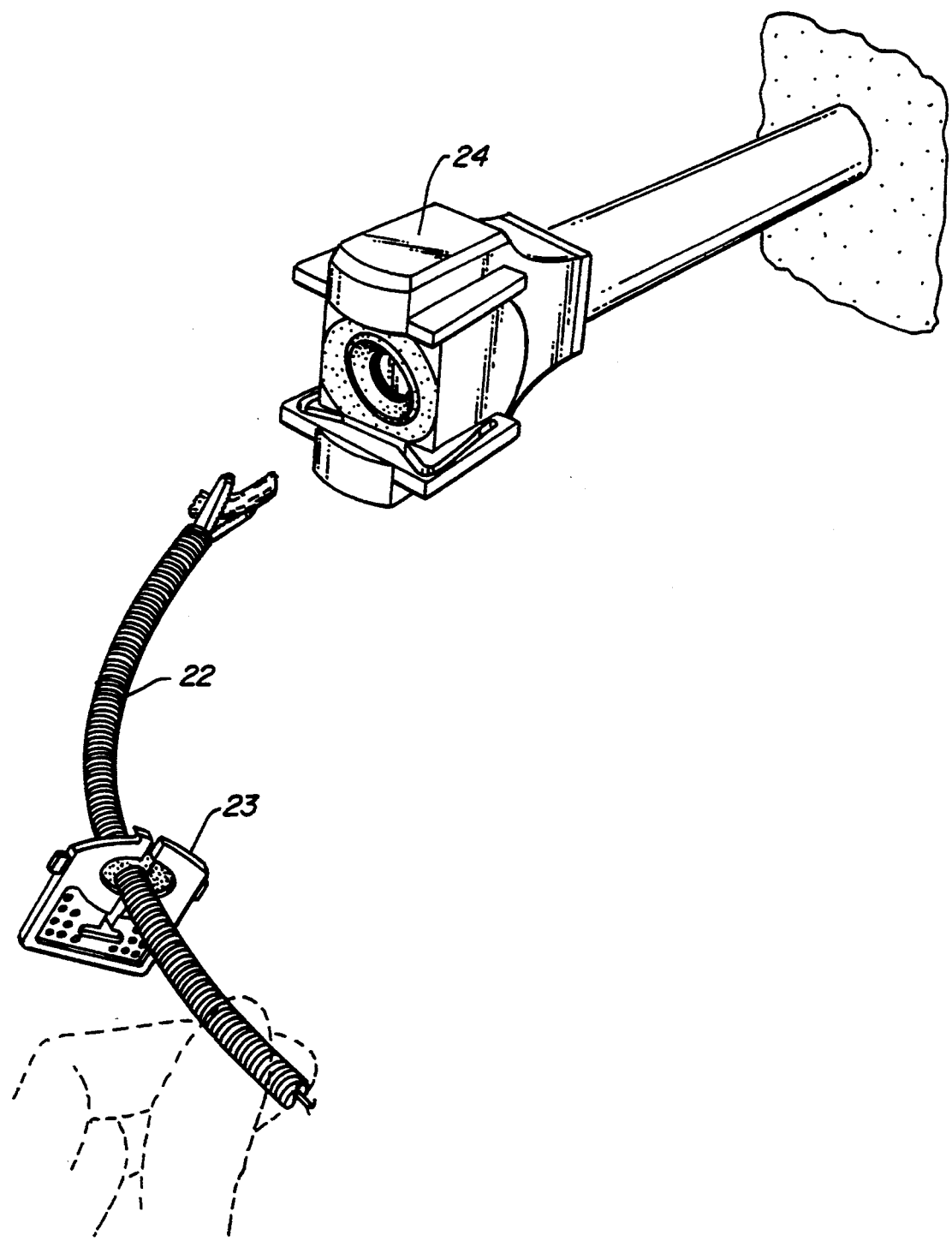
FIG. 3B shows the surgical instrument of FIG. 3A having been removed together with an adapter seal.

Referring to FIG. 3B, the adapter seal 23 has been removed from the cannula housing 24 and the tissue specimen 26 has been retrieved intact from the body. If desired, it is possible to continue the procedure by repositioning the adapter seal 23 back on the track or, alternatively, a second adapter seal (not shown) having a different aperture size can be moved into position for use with a different surgical instrument.

Figure 4:
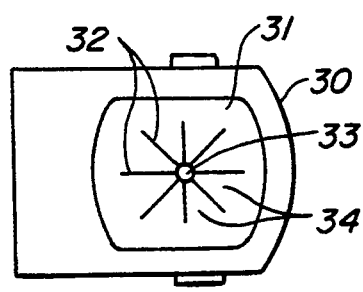
FIG. 4 is a front view of an embodiment of the present adapter seal having a sealing element having movable flaps.

Referring to FIG. 4, an alternative embodiment is shown for the adapter seal of the present invention. The adapter seal 30 has a sealing element 31 with several cuts 32 extending radially from the aperture 33 to form triangular flaps 34. In the preferred embodiment, the cuts 32 extend only partially into sealing element 31.

The depth of the cuts 32 are such that the silicone rubber material holding the flaps 34 together can be easily torn. When a large specimen is pulled through the aperture 33, the flaps 34 are pulled back thereby enlarging the passageway for a specimen to be drawn through. The flaps 34 separate along the radial cuts 32. The size of the triangular flaps 34 can be varied depending on the number of cuts 32 and the diameter of the cannula.

Figure 5A:
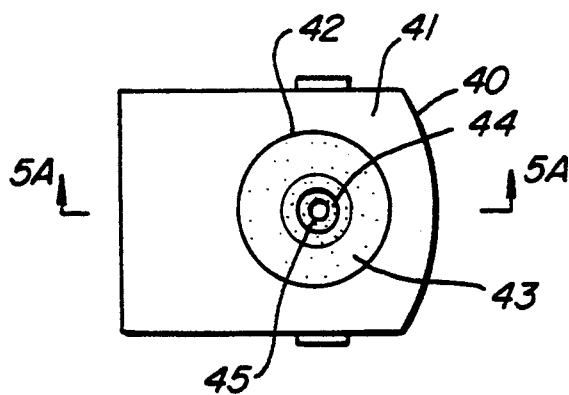
FIG. 5A is a front view of an embodiment of the present adapter seal having a removable washer-like part as a sealing element.
Figure 5B:
FIG. 5B is a cross-sectional view of the embodiment shown in FIG. 5A taken along the lines 5A—5A.

Referring to FIGS. 5A and 5B, an alternative embodiment is shown for the adapter seal of the present invention. The adapter seal 40 has a plate 41 opening 42 that accommodates a removable washer-like sealing element 43. The washer-like sealing element 43 is preferably made of a polyesterimide; for example, "Ultem." The sealing element 43 has a rubber gasket 44 that acts to form a seal around an aperture 45. The sealing element 43 is held in opening 42 of plate 41 by an adhesive paper 46 that has a tabbed portion 47. Once the adhesive paper 46 is removed, the sealing element 43 can be separated from the plate 41 and a specimen, which may be too large to pass through aperture 45, will be allowed to be drawn through the opening 42.

Figure 6A:
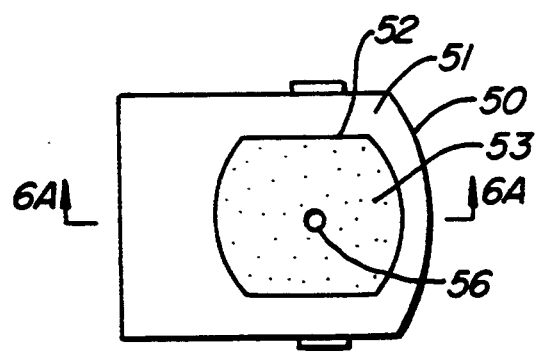
FIG. 6A is a front view of an embodiment of the present adapter seal having a removable gasket-like part as a sealing element.
Figure 6B:
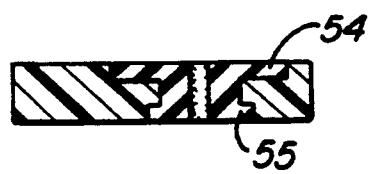
FIG. 6B is a cross-sectional view of the embodiment shown in FIG. 6A taken along the lines 6A—6A.

Referring to FIGS. 6A and 6B, another alternative embodiment is shown for the adapter seal of the present invention. The adapter seal 50 has an opening 52 in plate 51 that accommodates a gasket sealing element 53. The gasket 53 is preferably made of a silicone rubber material. The gasket sealing element 53 is held snugly in opening 52, but is not bonded to plate 51. The sealing element 53 has an aperture 56 for inserting a surgical instrument. Referring to FIG. 6B, the front flange portion 54 of the sealing element 50 is substantially larger than the back flange portion 55 of the sealing element. While large surface area on the front flange portion 54 prevent the sealing element 50 from being pushed through opening 51, the small back flange portion 55 is flexible and will allow the sealing element 50 to be pulled out when a large specimen is being extracted. Alternatively, the gasket 53 can be constructed of a plastic core and rubber molded around the core to form the aperture 56 and flanges 54 and 55.

It is within the scope of the present invention, although not shown in FIGS. 4, 5 and 6, to include a slot and openings defining arm portions in the plates of the alternative enbodiment adapter seals, as well as releasing means to permit these alternative embodiments of the adapter seal to be removable.

It is to be understood that while the invention has been described above in conjunction with the preferred specific embodiments, the description and examples are intended to illustrate and not limit the scope of the invention, which is defined by the scope of the appended claims.

What is claimed is:

1. An adapter seal in a cannula assembly for performing endoscopic procedures, said cannula assembly comprising a cannula having a proximal extracorporeal end and at least one track at said proximal end, said adapter seal being slidable along said track said adapter seal comprising:
   a sealing element having an aperture for receiving and providing a gas-tight fit around an elongated portion of a surgical instrument, said aperture being aligned with the longitudinal axis of said cannula during endoscopic procedures; and
   a plate accommodating said sealing element, said plate comprising engagement means for slidably engaging said track to permit said adapter seal to glide on said track, said engagement means being movable to allow said adapter seal to be removed from said track;
   wherein removal of said adapter seal permits the withdrawal of said surgical instrument from cannula while said surgical instrument is grasping a tissue specimen that is larger than said aperture.

2. An adapter seal according to claim 1 wherein said engagement means comprises at least two tabs, one of said tabs is on a top edge of said plate and another of said tabs is on a bottom edge of said plate.

3. An adapter seal according to claim 1 wherein said engagement means is wedge-shaped.

4. An adapter seal according to claim 1 wherein said track comprises a channel having side surfaces and said engagement means has at least one flat side surface for cofacial contact with one of said side surfaces of said track.

5. An adapter seal according to claim 1 further comprising tensioning means for maintaining said engagement means in said track, said tensioning means comprises arm portions defined by openings in said plate, said engagement means being located on said arm portion, said arm portions having releasing means extending therefrom and being displaceable by applying force to said releasing means.

6. An adapter seal according to claim 5 wherein said releasing means is a notch on one of said arm portions for manipulation of said arm portion.

7. An adapter seal according to claim 5 wherein said sealing element extends between said arm portions and provides tension against the displacement of said arm portions.

8. An adapter seal in a cannula assembly for performing endoscopic procedures, said cannula assembly comprises a cannula having a proximal extracorporeal end and at least one track at said proximal end, said adapter seal being slidable along said track, said adapter seal comprising:
   a sealing element having an aperture for receiving and providing a gas-tight fit around an elongated portion of a surgical instrument, said sealing element comprises movable flaps that separate along seams extending radially from said aperture, said aperture being aligned with the longitudinal axis of said cannula during endoscopic procedures; and
   a plate for accommodating said sealing element, said plate having engagement means for slidably engaging said track;
   wherein said movable flaps extend outward from said proximal end to permit the withdrawal of said surgical instrument from cannula while said surgical instrument is grasping a tissue specimen that is larger than said aperture.

9. An adapter seal according to claim 8 wherein said plate further comprises arm portions defined by openings in said plate, said engagement means being located on said arm portions, said arm portions having releasing means extending therefrom and being displaceable by applying force to said releasing means.

10. An adapter seal in a cannula assembly for performing endoscopic procedures, said cannula assembly comprises a cannula having a proximal extracorporeal end and at least one track at said proximal end, said adapter seal being slidable along said track, said adapter seal comprising:
   a removable washer-like sealing element comprising an aperture for receiving a surgical instrument and a sealing means in said aperture for providing a gas-tight fit around an elongated portion of said surgical instrument, said aperture being in alignment with the longitudinal axis of said cannula during endoscopic procedures; and a plate comprising an sitted opening for accommodating said sealing element, a removable adhesive paper holding said sealing element in said sitted opening and engagement means for slidably engaging said track;

wherein the removal of said sealing element permits the withdrawal of said surgical instrument from cannula while said surgical instrument is grasping a tissue specimen that is larger than said aperture.

11. An adapter seal according to claim 10 wherein said plate further comprises arm portions defined by openings in said plate, said engagement means being located on said arm portions, said arm portions having releasing means extending therefrom and being displaceable by applying force to said releasing means.

12. An adapter seal in a cannula assembly for performing endoscopic procedures, said cannula assembly comprises a cannula having a proximal extracorporeal end and at least one track at said proximal end, said adapter seal being slidable along said track, said adapter seal comprising:

a removable gasket sealing element comprising an aperture for receiving and providing a gas-tight fit around an elongated portion of a surgical instrument, and a front and back flanged portions, said front flange portion being larger than said back flange portion, said back flange being made of flexible material, said aperture being aligned with the longitudinal axis of said cannula while performing endoscopic procedures; and a plate accommodating said sealing element, said plate having engagement means for engaging said track;

wherein the removal of said sealing element permits the withdrawal of said surgical instrument from cannula when said surgical instrument is grasping a tissue specimen that is larger than said aperture.

13. An adapter seal according to claim 12 wherein said plate further comprises arm portions defined by openings in said plate, said engagement means being located on said arm portions, said arm portions having releasing means extending therefrom and being displaceable by applying force to said releasing means.

14. A cannula assembly comprising:

a cannula;

a cannula housing at a proximal extracorporeal end of said cannula, said housing having parallel peripheral tracks and at least one adapter seal;

said adapter seal comprising a plate accommodating a sealing element, said sealing element having an aperture that is aligned with the longitudinal axis of said cannula during endoscopic procedures;

said plate comprising engagement means for slidably engaging said track, arm portions providing tension for maintaining said engagement means in said track, said engagement means being located on said arm portions; and releasing means extending from said arm portions, wherein said engagement means are disengaged from said track by applying a force to said release means.

15. A cannula assembly according to claim 14 further comprising a plurality of said adapter seals, each adapter seal being slidable and having an aperture sized to accommodate a different surgical instrument.

16. A cannula assembly according to claim 14 wherein said sealing element of said adapter seal has movable flap portions.

17. A cannula assembly according to claim 14 wherein said sealing element is removable washer-like seal that is sitted in an opening in said plate, said sealing element being held-in place by a removable adhesive paper.

18. A cannula assembly according to claim 14 wherein said sealing element is a removable annular gasket having a front and back flange portions wherein said front flange is larger than said back flange and said back flange is made of flexible material.

19. A trocar assembly for performing an endoscopic procedure comprising:

a trocar having a handle and an obturator shaft with a sharp distal end;

a cannula assembly comprising a cannula, a cannula housing at a proximal extracorporeal end of said cannula, said housing having a peripheral track and at least one adapter seal slidably engaging said track; said adapter seal comprising a plate accommodating a sealing element having an aperture for receiving and providing a snug fit around a surgical instrument, said aperture being aligned with the longitudinal axis of said cannula while performing endoscopic procedures;

said plate comprising engagement means for engaging said track, and tensioning means for holding said engagement means in said track, and releasing means for applying a countering-force against said tensioning means to disengage said engagement means from said track; and said trocar being insertable into said proximal extracorporeal end of said cannula assembly when said adapter seal is positioned on a side of said cannula housing.

20. A method for performing an endoscopic procedure using a trocar assembly comprising a trocar and a cannula assembly, said trocar having an obturator shaft with a sharp distal end and a handle at the proximal end, said cannula assembly having a cannula and a cannula housing at aproximal extracorporeal end of said cannula, said cannula housing includes a peripheral track for slidably engaging at least one adapter seal, said adapter seal comprising a plate accommodating a sealing element having a suitably sized aperture, said plate having tensioning means for holding engagement means in said track, said adapter seal having releasing means for disengaging said engagement means from said track, said method comprising the steps of:

(a) making an incision into a body cavity with said trocar assembly using said sharp distal end of said obturator shaft;

(b) inserting a distal end of said cannula into said body cavity;

(c) removing said trocar from said cannula assembly;

(d) moving said adapter seal on said cannula housing on said track into position over an openable end of said cannula housing at said proximal extracorporeal end, said aperture being in alignment with the longitudinal axis of said cannula;

(e) inserting a surgical instrument having an elongated portion with a first diameter and function end through said aperture in said sealing element of said adapter seal and through said cannula into said body cavity, said aperture forming a snug fit around said elongate portion;

(f) using said surgical instrument to perform said endoscopic procedure;

(g) removing said adapter seal from said cannula assembly by applying a force to said releasing means to disengage said engagement means from said track;

(h) withdrawing said surgical instrument from said cannula assembly with said adapter seal attached to said elongate portion.

21. A method according to claim 20, further comprising the step of:

(i) moving a second adapter seal on said cannula housing on said track into position over said openable end of said cannula housing at said proximal extracorporeal end.

22. A method according to claim 20 wherein the sealing element is removed from said plate to allow said surgical instrument to be removed.

* * * * *